United States Patent
Kulkarni (10) Patent No.: US 9,816,803 B2
(45) Date of Patent: Nov. 14, 2017

(54) METHOD AND SYSTEM FOR LOW COHERENCE INTERFEROMETRY

(71) Applicant: Manish Dinkarrao Kulkarni, Pleasanton, CA (US)

(72) Inventor: Manish Dinkarrao Kulkarni, Pleasanton, CA (US)

(73) Assignee: NETRA SYSTEMS, INC., Pleasanton, CA (US)

( * ) Notice: Subject to any disclaimer, the term of this patent is extended or adjusted under 35 U.S.C. 154(b) by 0 days.

(21) Appl. No.: 15/054,050

(22) Filed: Feb. 25, 2016

(65) Prior Publication Data

US 2016/0178346 A1    Jun. 23, 2016

Related U.S. Application Data

(63) Continuation-in-part of application No. 14/302,366, filed on Jun. 11, 2014, now abandoned, and a continuation-in-part of application No. 13/723,006, filed on Dec. 20, 2012, and a continuation-in-part of application No. 12/941,991, filed on Nov. 8, 2010, now Pat. No. 8,797,551, said application No. 13/723,006 is a continuation-in-part of application No. 12/732,484, filed on Mar. 26, 2010, now abandoned, said application No. 14/302,366 is a continuation-in-part of application No. 12/706,717, filed on Feb. 17, 2010, now abandoned.

(60) Provisional application No. 61/259,294, filed on Nov. 9, 2009, provisional application No. 61/153,893, filed (Continued)

(51) Int. Cl.
*G01B 9/02* (2006.01)
*A61B 3/10* (2006.01)
*G01N 21/47* (2006.01)
*G01N 21/49* (2006.01)
*A61B 3/107* (2006.01)

(52) U.S. Cl.
CPC .......... *G01B 9/02091* (2013.01); *A61B 3/102* (2013.01); *G01B 9/02027* (2013.01); *G01B 9/02044* (2013.01); *G01N 21/4795* (2013.01); *G01N 21/49* (2013.01); *A61B 3/107* (2013.01); *G01B 2290/35* (2013.01); *G01B 2290/65* (2013.01)

(58) Field of Classification Search
CPC ........................ G01B 9/02044; G01N 21/4795
USPC ........................................................ 356/477
See application file for complete search history.

(56) References Cited

U.S. PATENT DOCUMENTS 6,424,466 B1 *  7/2002  Flanders .................... G01J 3/26
                                                              356/519
8,797,551 B2 *  8/2014  Kulkarni ................ A61B 3/102
                                                              356/521

(Continued)

*Primary Examiner* — Jonathan Hansen (57) ABSTRACT

Optical Coherence Tomography (OCT) system and apparatus of this instant application is very useful for diagnosis and management of 3ophthalmic diseases such as retinal diseases and glaucoma etc. Instant innovative OCT diagnostic system leverages advancements in cross technological platforms. The Michelson interferometric system presented in this application could be used for the OCT imaging, which includes biological OCT imaging, medical OCT imaging, ophthalmic OCT imaging, corneal OCT imaging, retinal OCT imaging, and the like. A tunable filter is placed in front of the detector to make the interferometer more sensitive and accurate for examining various samples for diagnosis.

20 Claims, 6 Drawing Sheets

Related U.S. Application Data on Feb. 19, 2009, provisional application No. 61/163,872, filed on Mar. 27, 2009.

(56) References Cited

U.S. PATENT DOCUMENTS

| | | | |
|---|---|---|---|
| 2003/0025917 A1* | 2/2003 | Suhami | A61B 3/102 356/601 |
| 2003/0231692 A1* | 12/2003 | Belikov | G02B 5/1828 372/102 |
| 2006/0103850 A1* | 5/2006 | Alphonse | A61B 5/0066 356/479 |
| 2007/0024856 A1* | 2/2007 | Izatt | A61B 3/102 356/456 |

* cited by examiner

METHOD AND SYSTEM FOR LOW COHERENCE INTERFEROMETRY

REFERENCE TO CROSS RELATED APPLICATIONS

The instant application is a continuation-in-part application and claims priority to the U.S. patent application Ser. No. 14/302,366 (filed on Jun. 11, 2014), which claims priority to now patented (U.S. Pat. No. 8,797,551) U.S. application Ser. No. 12/941,991 filed on Nov. 8, 2010 and U.S. application Ser. No. 13/723,006 filed on 20 Dec., 2012. The disclosure is hereby incorporated by this reference in its entirety for all of its teachings.

FIELD OF THE INVENTION

The present invention relates to the field of optical measurement devices. More particularly, the present invention relates to the field of optical test and measurement, optical ranging and imaging of a specimen using optical coherence tomography or low coherence interferometry or white-light interferometry.

BACKGROUND OF THE INVENTION

Optical coherence tomography ("OCT") is a technology that allows for noninvasive, cross-sectional optical imaging in biological as well as non-biological media with high spatial resolution and high sensitivity. OCT is an extension of low coherence or white-light interferometry, in which a low temporal coherence light source is utilized to obtain precise localization of reflections internal to a probed structure along an optic axis (i.e., as a function of depth into the sample). An optical beam is directed at the tissue, and a small portion of this light that reflects from sub-surface features is collected. In an OCT instrument, an optical interferometer is used in such a manner as to detect only coherent light. In the process, the depth and the intensity of the light reflected from a sub-surface feature is obtained. A three-dimensional image can be built by scanning, as in a sonar or radar system. The most commonly used interferometers in these devices are Michelson interferometer and Mach-Zehnder interferometer (MZI), which are well-known.

Typical OCT imaging systems comprise a Michelson Interferometer. The signal is detected by a grating based spectrometer equipped with a linear detector array (or a line-scan camera). Further, OCT interferometric systems known in the art are complex in arranging optical devices, expensive and are not portable.

SUMMARY

In view of the foregoing disadvantages inherent in the prior art, the general purpose of the present invention is to provide a novel compact, affordable optical test, measurement or imaging device that is configured to include all advantages of the prior art, and to overcome the drawbacks inherent therein.

In one embodiment, a novel compact, affordable optical test, measurement or imaging device used for detection, imaging of ocular structures and pathology in diagnostic, diagnosis and pathogenesis is disclosed.

In another embodiment, a spectral-domain interferometric system that comprises a Michelson interferometer, and an optical system laterally scanning the specimen is disclosed.

Here and in the rest of the specifications, laterally scanning means scanning the beam in a direction perpendicular to the beam. Such a direction can be called x or y or any direction in x-y plane. Such lateral scanning provides multi-dimensional imaging as well as multi-dimensional metrology and multi-dimensional measurements. Lateral scanning can provide 2-dimensional or 3-dimensional images; 2-dimensional or 3-dimensional measurements; 2-dimensional or 3-dimensional metrology. Such lateral scanning also permits optical coherence tomography (OCT) imaging.

In another embodiment, an interferometric system comprises a Michelson interferometer, a frequency (i.e., wavelength)-tunable detector and optionally a lateral scanning (of the specimen) mechanism. A tunable detector as defined in this invention comprises of a tunable filter (preceding the detector), which separates the input broad-band light into light with narrow-band-wavelengths and outputs them sequentially at different time intervals in a single output fiber.

In an aspect of the present invention, an interferometric system for imaging a biological sample or a scattering medium is provided. The interferometric system comprises a broadband light source, a plurality of beam splitters, a plurality of mirrors, a sample, a lateral scanning optical system, a tunable filter, a detector and a data processing system.

In another aspect of the present invention, a method for generating a tomographic image of a sample is provided. The method includes light from the broadband light source that is operating at a suitable center wavelength enters into a Michelson interferometer, where it gets separated into a sample arm and a reference arm using an optic beam splitter. A light from the reference arm gets reflected by mirror and returns to the beam splitter. A light from the sample arm enters into the sample by means of a lateral scanning optical system, and the back scattered light from the sample returns to beam splitter (typically, but not limited to, 50% reflectance, 50% transmittance) through the lateral scanning optical system. The light from the sample and reference arms interfere with each other at the beam splitter before entering a tunable filter that wavelength-division-multiplexes the interfered light, and then finally enters into a detector for analysis. Wavelength-division-multiplexing as defined in this invention is a process of separating the input broad-band light into light with narrow-bands-with various center-wavelengths and outputting them sequentially at different time intervals in a single output fiber.

These together with the other aspects of the present invention, along with the various features of novelty that characterized the present invention, are pointed out with particularity in the claims annexed hereto and form a part of the present invention. For a better understanding of the present invention, its operating advantages, and the specified object attained by its uses, reference should be made to the accompanying drawings and descriptive matter in which there are illustrated exemplary embodiments of the present invention.

BRIEF DESCRIPTION OF THE DRAWINGS

Understanding of the present invention will be facilitated by consideration of the following detailed description of the preferred embodiments of the present invention taken in conjunction with the accompanying drawings, in which like numerals refer to like parts and in which.

Other features of the present embodiments will be apparent from the accompanying figures and from the detailed description that follows.

DETAILED DESCRIPTION OF THE INVENTION

The present invention proposes an interferometric system for optical imaging, which is one of the major needs for refractive surgery, ophthalmic applications, corneal imaging, retinal imaging, endoscopic/catheter imaging, dental imaging etc. In particular, the invention is an integrated system for detection, ranging, metrology and multi-dimensional imaging.

Figure 1:
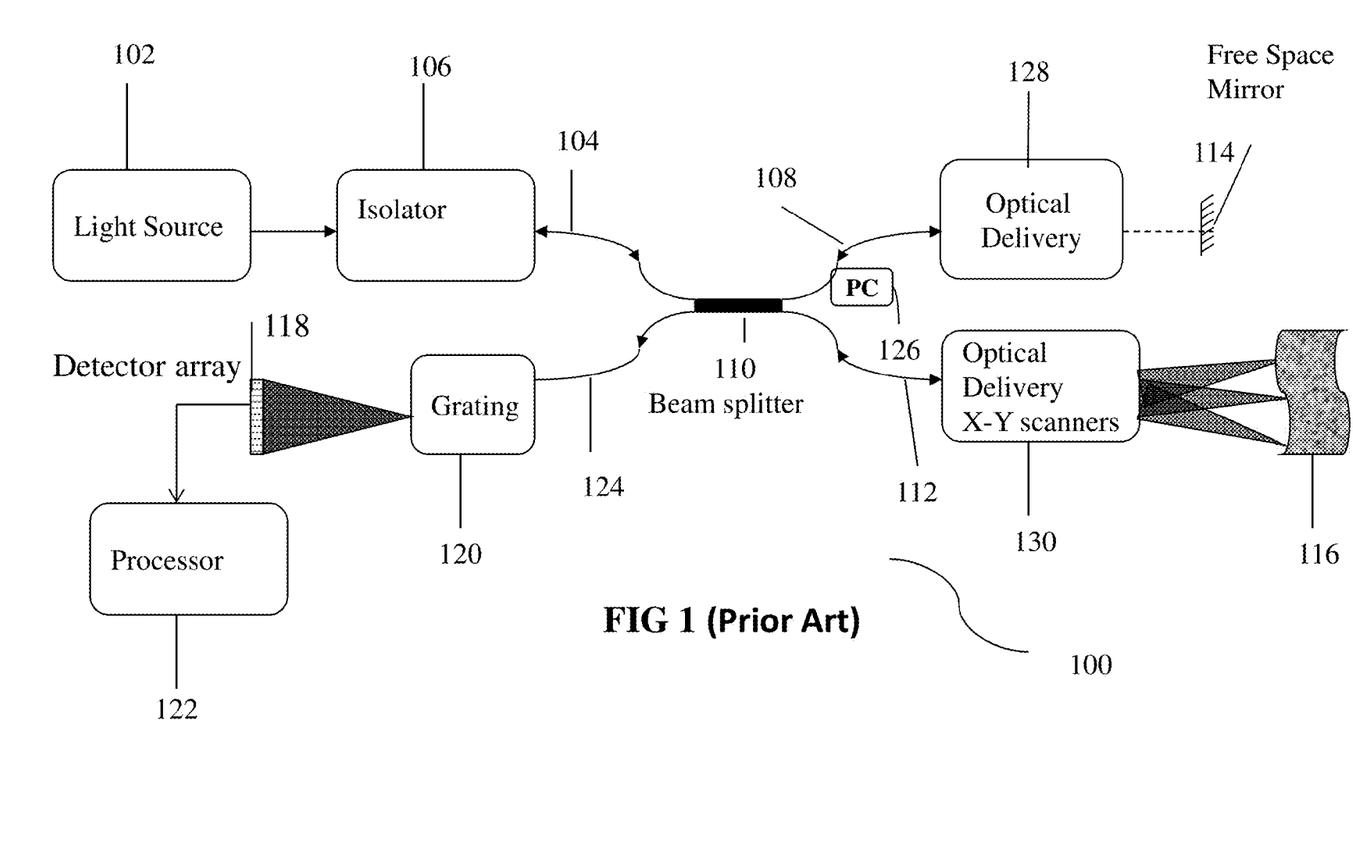
FIG. 1 illustrates an optical diagram of a Michelson Interferometric optical coherence tomography apparatus and system as known in the art.

FIG. 1 illustrates a schematic figure of a Michelson Interferometric optical coherence tomography system (100) as known in the art. The interferometer (100) has a light source (102) operating at a suitable center wavelength and a suitable bandwidth. Some light sources may be sensitive to light reflected back from the interferometer. In order to protect such light sources, an optional isolator (106) may be used. The isolator absorbs the light received from the fiber optic beam splitter (110), and it stops the light from entering the source 102. In the interferometer, the source light is separated into the sample and reference arms using a fiber optic beam splitter (110). The beam-splitter 110 could also be a free-space beam-splitter for a free-space interferometer. The beam splitter is typically 50/50. The beam-splitter comprises of 4 arms. The source arm 104, which receives the light from the source and directs it to the beam-splitter to split the light into the reference arm 108 and the sample arm 112. The light returning from the reference and sample arms combines in the beam splitter and the light gets separated into the source arm (104) and the reflected sample arm or detector arm (124). The isolator absorbs the light received from the fiber optic beam splitter (110), and it stops the light from entering the source 102. The sample arm (108) comprises of a probe, which focuses light into the sample (116) using lateral Scanning Optical System unit (130) with x-y scanner and collects the backscattered light. The light in the detector arm is detected by a grating (120) based spectrometer equipped with a linear detector array (or a line-scan camera 118). The data from the camera or array is transferred to a processor 122, which is typically a desk-top computer.

In some existing systems, if the beam-splitter 110 is fiber-optic, the means to adjust polarization are used in the form of a fiber optic polarization compensator (PC) (126), which is made up of fiber optic loops, in the reference arm 108 to match the polarization in both the sample and reference arms. Such matching provides optimal interference signal strength. The PC 126 could be placed either in the sample arm or the sample arm.

Figure 2:
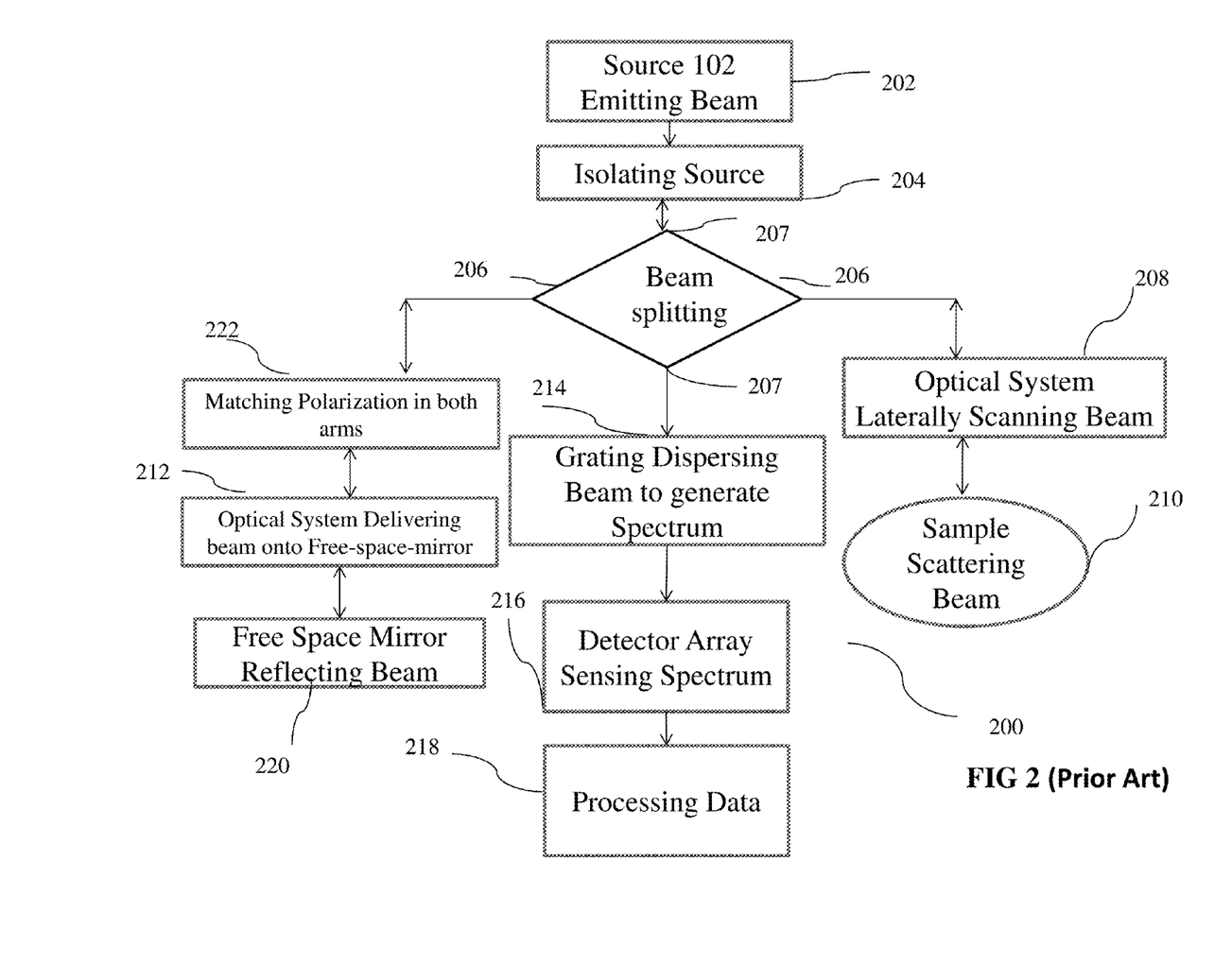
FIG. 2 is a flow chart illustrating a Michelson Interferometric optical coherence tomography system as known in the art.

FIG. 2 is a flow chart (200) illustrating an Optical Coherence Tomography (OCT) measurement system based on a Michelson interferometer as known in the art. As illustrated, methodology starts at step (202), wherein the source 102 emits a beam of light which optionally passes through an isolator at step 204. While the apparatus, system and method would work for both broad-band and narrow-band light, a broad-band light is preferred for OCT. The beam passes a first beam splitter (110) (typically 50/50) at step (206) getting divided into two separate light beams known as reference arm (108) and sample arm (116). The light returning from the sample and reference arms is also received at step 206 and separates into the source arm (104) and detector arm (124). In the reference arm 108, at step 222, the polarization is optionally matched using a polarization compensator PC (126) in the reference arm in order to provide optimal interference signal strength. The fiber optic polarization compensator (PC) (126) is made up of fiber optic loops. The PC 126 could be placed either in the sample arm or the reference arm.

At step 212, an optical delivery system (128) delivers the light beam onto a free-space-mirror (114) in the reference arm. The free-space-mirror reflects back the light beam to the optical delivery system at step 220. The light from the reference arm returns to the beam splitter 110 at step 206 and splits into source arm and detector arm at step 207. In the sample arm 112, at step (208), the beam passes through lateral scanning optical delivery system (130), it comprises of x-y scanner) and falls upon the sample at step (210). The sample arm beam is reflected and/or scattered back after it strikes the sample and returns to the beam splitter 110 and splits into source arm and detector arm at step 207. The light returning from the reference arm (108) and sample arms (112) interferes at step (207); known as the interference light beam entering the detector arm 124. The light beam is dispersed by a grating (120) at step 214. The dispersed light, also called a spectrum is sensed by an array of detectors (118), at step 216. The components 118 and 120 form a spectrometer sub-system, and optionally may comprise of lenses, mirrors and/or other optical components to facilitate optical beam propagation and maximize optical signal. The spectral data measured by the detector array are transferred to a processor (122), typically a computer, for further processing at step 218. The data may be transferred by a USB cable, or a camera-link cable or an Ethernet cable.

Figure 3:
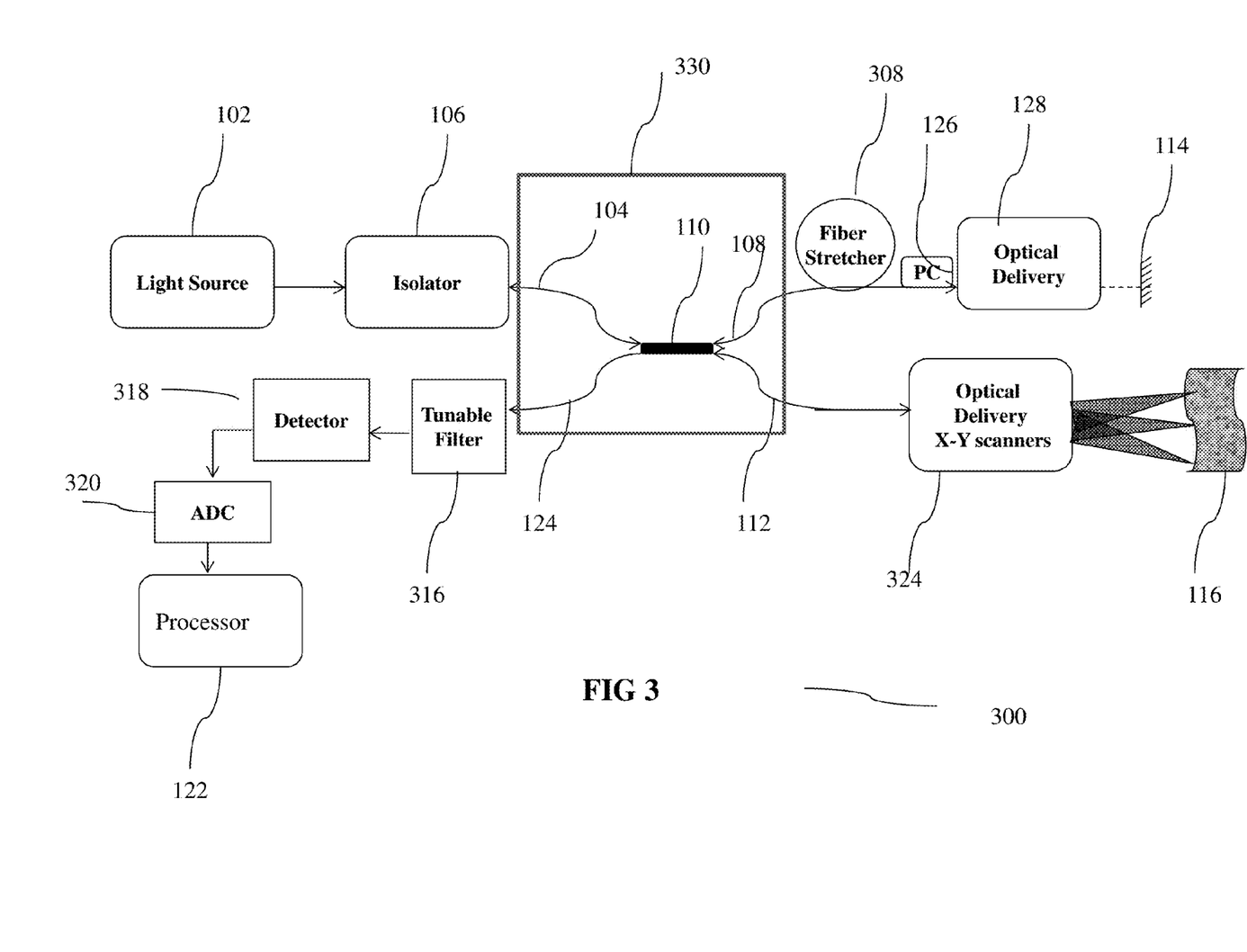
FIG. 3 illustrates an optical diagram of a Michelson Interferometer apparatus and system configured with a tunable filter in accordance with an embodiment as disclosed.

FIG. 3 illustrates an optical diagram of a Michelson Interferometric optical coherence tomography system (300), in accordance with an embodiment of the present invention. Most components are similar to the system described in FIG. 1. Fiber stretcher 308 comprises of a fiber looped around a piezoelectric device (which is a solid block that can be expanded or contracted by electric voltage). The purpose of a fiber stretcher is to increase or decrease the path-length in the reference arm of the interferometer by increasing or decreasing the fiber-length. Although the fiber stretcher 308 is shown in the reference arm, it can be placed either in the reference arm or sample arm. If the fiber stretcher 308 is kept in the reference arm, since the fiber is looped around the piezoelectric device, care must be taken to provide extra fiber in the sample arm so that the sample arm and reference arm path lengths are matched. According to one more embodiment, the Michelson interferometric system comprises of a means to adjust polarization in the sample arm (112) to match the polarization in the reference arm (108) to achieve optimal signal strength.

According to an embodiment of the instant invention, the light in the detector arm 124 enters a tunable filter (316) for wavelength-division-multiplexing. Wavelength-division-multiplexing as defined in this invention is a process of separating the input broad-band light into light with narrow-bands with various center-wavelengths and outputting them sequentially at different time intervals in a single output fiber.

This tunable filter (316) can be e.g., (by example, but not limited to) a Fabry Perot interferometer tunable filter or a tunable filter based on a programmable-grating-based filter or an acousto-optic tunable filter or a grating based tunable filter or any other interference filter. The multiplexed data are detected by a detector (318), are digitized by an analog to digital converter (ADC) 320, and are forwarded to a data processing unit or a processor (320) for analyzing the data. A tunable filter as defined in this invention separates the input broad-band light into light with narrow-band- ("tuned") wavelengths and outputs them sequentially at different time intervals in a single output fiber.

According to one more embodiment, the Michelson interferometric system may be used as a multi-dimensional metrology system by laterally scanning the beam incident on at least one sample (116) by means of an optical system 324. Per one more embodiment, the lateral scanning in the optical system 324 is achieved by using a micro electro mechanical system (MEMS) or micro-opto-mechanical system (MOMS) mirrors and lenses in the Michelson interferometric system. The lateral scanning in the optical system 324 could also be achieved by traditional galvanometric mirrors. All the major components of the Michelson interferometer including 110, 104, 108,124, 112, form an interferometer sub-assembly 330. A Michelson interferometer can be built using a photonic integrated circuit using waveguides as described in F. Morichetti, et. al. (2007), and Duc Nguyn et al (2013). The technology is based on $Si_3N_4$ and $SiO_2$ waveguide technology called TriPleX™, which has been developed by LioniX BV (Enschede, The Nederlands) as described in the article above by Morichetti et al. In an embodiment the interferometer sub-assembly 330 can be a photonic integrated assembly.

In an embodiment, the interferometric paths comprise of $Si_3N_4$ and $SiO_2$ waveguides.

In another embodiment, the interferometric apparatus is a photonic integrated circuit.

The fiber components 108, 104, 124 and 112 would turn into waveguides in such an integrated assembly. The lengths of waveguides 108 and 112 can be adjusted to match the path-lengths in the reference and sample arms. Fiber stretcher 308 can optionally be used. The polarization compensator PC 126 need not be a part of this integrated circuit. PC is needed primarily for fiber-optic interferometer, and can be used if there is an optical-fiber in the system even after using the integrated circuit. The Photonic integrated circuits can be built using many types of material system by way example, but not by limitation; silica on silicon, lithium niobate electro-optic crystals, Silicon on insulator, many polymers, semiconductor materials such as GaAs & InP.

In an embodiment, the Michelson interferometric system design results in reducing the size of the system to form a compact or portable system or an embedded single integrated circuit (i.e., a system on chip (SOC)). Thus the interferometric system can be made a compact, portable system using an embedded single integrated circuit. The photonic integrated circuit described above can comprise of the Michelson interferometer 330, and tunable filter 316. The light source 102, the detector 318, could also be optionally included on the same photonic circuit. The isolator 106, the ADC 320 and the processor 122 could also be included in the same integrated circuit or the same chip. The isolator 106, the ADC 320 and the processor 122 and the interferometer could also be built using separate chips, which communicate with each other.

Figure 4:
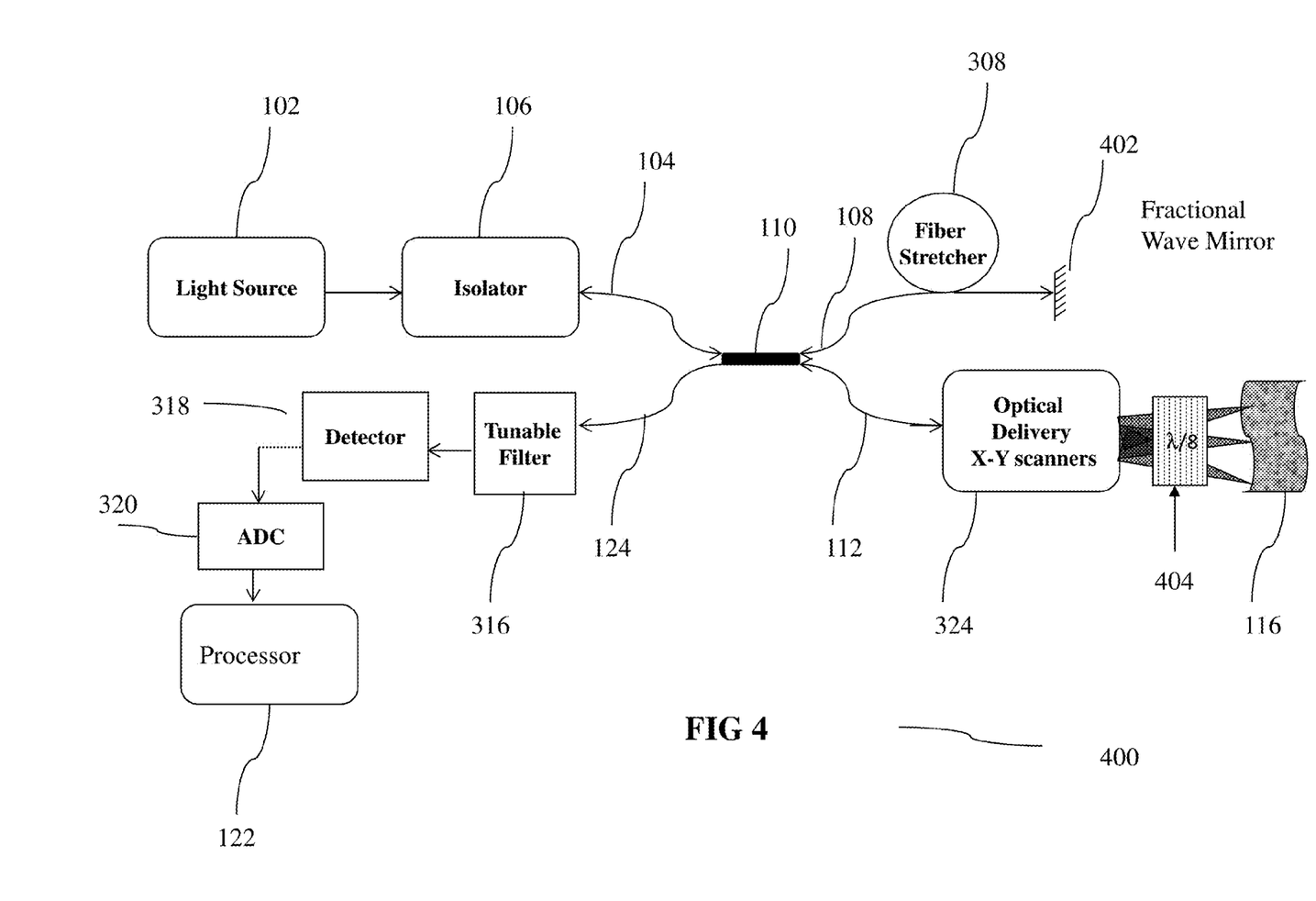
FIG. 4 illustrates an optical diagram of a Michelson Interferometer apparatus and system configured with a tunable filter, a waveplate and a Fractional Wave mirror in accordance with an embodiment as disclosed.

FIG. 4 illustrates an optical diagram of a Michelson Interferometric optical coherence tomography system (400), in accordance with an embodiment of the present invention. Most components are similar to those in the system described in FIG. 3. A birefringent mirror is used in the reference arm, and hence the polarization compensator is not needed. This birefringent mirror 402 can be a Fractional wave mirror 402, in accordance with the present invention. U.S. patent application Ser. No. 13/723,006 (to which we claim priority) describes this component in detail and we herewith incorporate it as a reference. The sample (116) can be any one of retina, skin, anterior segment of the eye, posterior segment of the eye, gastrointestinal tract, lungs, teeth, blood vessels, subsurface area of semi-conductors, chip manufacturing and sensitive medical equipment. The specimen 116 can be a biological sample or a scattering medium.

Such a fractional wave-plate can be built using an optical fiber. Mechanical stress on the fiber causes birefringence in the fiber. Stress can be generated by simply bending the fiber.

As described in U.S. patent application Ser. No. 13/723,006, the fractional wave mirror comprises of a fiber-optic mirror preceded by a fractional [45 degrees ($\lambda/8$)] waveplate. The polarization of light incident on the wave plate is rotated by 45 degrees, and is directed to the mirror. The reflected light is further rotated by 45 degrees by the fractional [45 degrees ($\lambda/8$)] waveplate and hence the resulting polarization is orthogonal to the incident polarization.

In some embodiments, the reference arm path is an optical fiber terminated by a fiber integrated mirror instead of a birefringent mirror (402).

In some embodiments, one can include by way of example but not by limitation a 45 degrees $\lambda/8$ wave plate 404 in the sample arm before the light is incident on the sample 116. The $\lambda/8$ wave plate may be placed in the sample arm just before the light is incident on the optical delivery unit 324. Since the polarization of the retro reflected light will be almost orthogonal to the incident light (considering the fact that the birefringence in the specimen 116 will modify the polarization state), the birefringence effects in the sample arm fiber 112 of the interferometer 400 will get cancelled. In a preferred embodiment, the $\lambda/8$ waveplate 404 is constructed using fiber optic components.

The effect of fiber-birefringence phenomenon (affecting the polarization of the light in the sample and reference arms) gets minimized due to arrangement of the birefringent mirror in the reference arm and $\lambda/8$ wave plate in the sample arm. Therefore, polarization in the sample and reference arms is closely matched, and a separate polarization compensator is not needed. According to one embodiment, the Michelson interferometric system 300 comprises of a beam-splitter (110) which can be a fiber-optic coupler. According to another embodiment, the Michelson interferometric system 300 comprises of, the reference arm path, which is an optical fiber terminated by a fiber integrated mirror instead of free-space-mirror.

Figure 5:
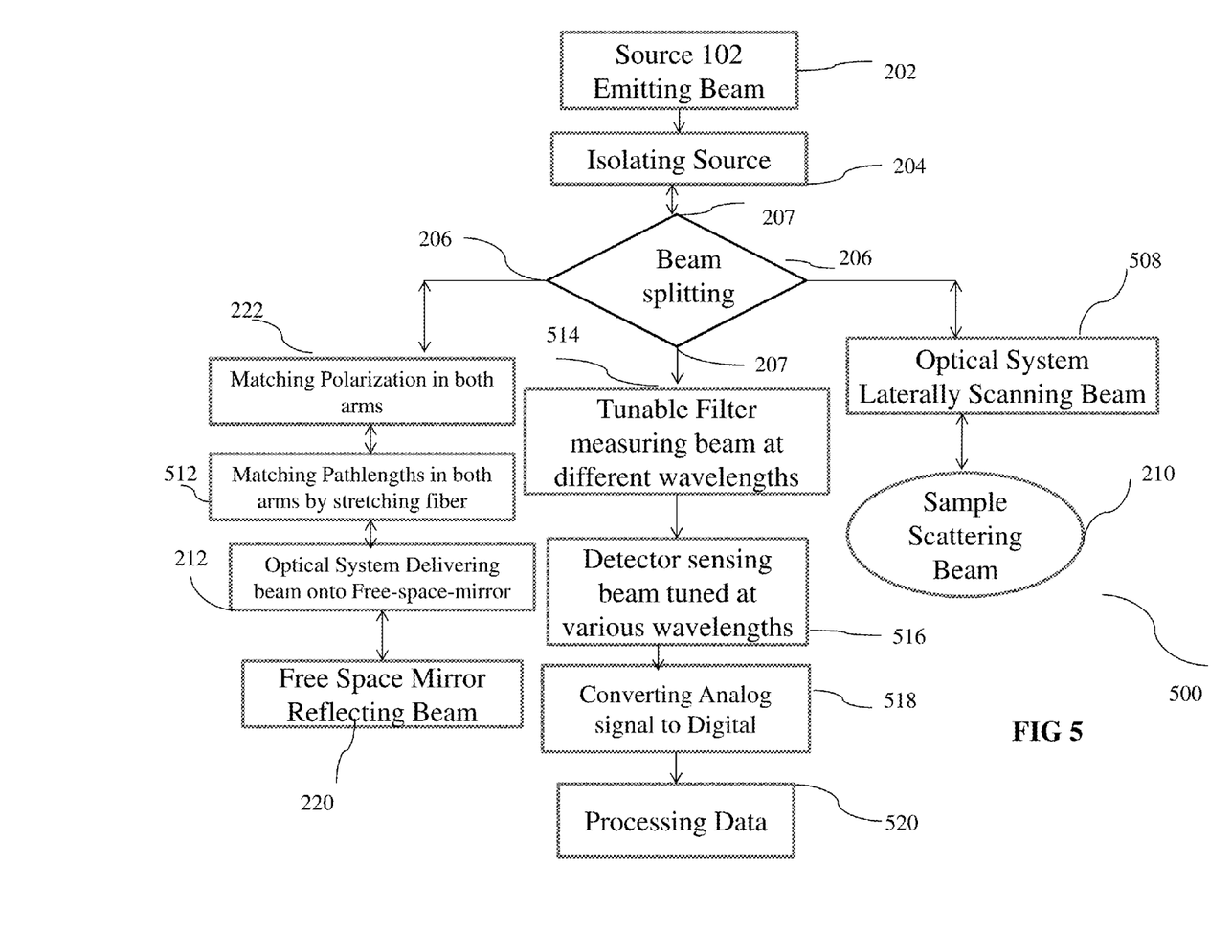
FIG. 5 is a flow chart illustrating a Michelson interferometric system configured with a wavelength-tunable filter to analyze the sample in accordance with an embodiment as disclosed.

FIG. 5 is a flow chart 500 of method of using the Michelson Interferometer apparatus in FIG. 3. Most steps are similar to the flow-chart in FIG. 2. However, we highlight the novel steps. The beam returning from the reference arm (108) and sample arm (112) interferes at step (207); known as interfered light beam or the interference light beam entering the detector arm 124. At step (508), the beam passes through lateral scanning optical delivery system (324, it comprises of x-y scanner) and falls upon the sample at step (210). Per one more embodiment, the lateral scanning in the optical system 324 is achieved by using a micro electro mechanical system (MEMS) or micro-opto-mechanical system (MOMS) mirrors and lenses in the Michelson interferometric system. The interfered light or the interference light beam in the detector arm enters a tunable filter (316) at step (514) where wavelength division multiplexing of interfered light beam (124) takes place. The multiplexed data are sensed by a detector 318 at step (516) and are digitized by an analog to digital converter (ADC) 320 at step 518, and are forwarded to a data processing unit or a processor (320) for analyzing the data at step 520.

This tunable filter can be e.g., (by example, not by limitation) a Fabry Perot interferometer tunable filter or an acousto-optic tunable filter or a grating based tunable filter or any other interference filter. A tunable filter as defined in this invention separates the input broad-band light into light with narrow-band-("tuned") wavelengths and outputs them sequentially at different time intervals in a single output fiber.

Figure 6:
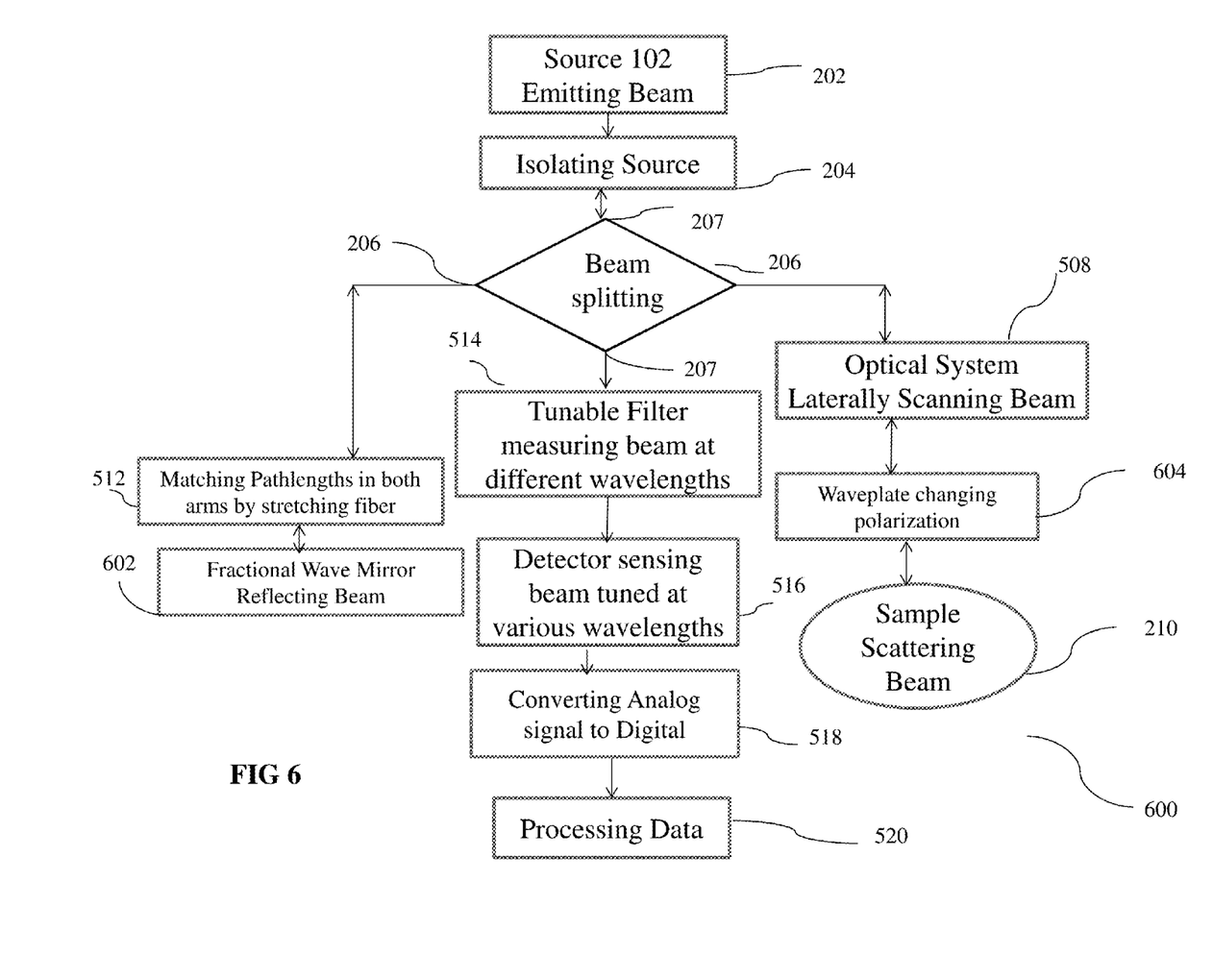
FIG. 6 is a flow chart illustrating a Michelson interferometric system configured with a wavelength-tunable filter, a waveplate and a Fractional Wave mirror in accordance with an embodiment as disclosed.

FIG. 6 is a flow chart 600 of a method of using the Michelson Interferometer as an apparatus in FIG. 4. Most steps are similar to the flow-chart in FIG. 5. Here we highlight the unique steps and differences. In the reference arm, step 212 of polarization compensation is not needed due to step 602 of the fiber optically integrated birefringent reference mirror (402) or the Fractional Wave Mirror (402) reflecting the beam. Since the mirror 402 is fiber-optically integrated, the step 212 of delivering the beam onto a free-space mirror is not needed.

In the sample arm, an additional step 604 of the $\lambda/8$ wave plate 404 changing the polarization is introduced. The light exiting optical system 508 enters the waveplate in step 604, changing the polarization. Thus, step 604 comprises of light passing through a waveplate in the sample arm. While the step 604 is shown after the step 508, it can be performed before or after the step 508. The beam exiting the waveplate is incident on the sample in step 210. In another embodiment (not shown), the beam exiting sample arm fiber 112 enters the waveplate 404 in step 604. The beam exiting the waveplate 404 is incident on the optical delivery system 324 (laterally scanning the beam) in step 508. The beam exiting the optical delivery system 324 is incident on the sample in step 210. The sample (116) can be any one of retina, skin, anterior segment of the eye, posterior segment of the eye, gastrointestinal tract, lungs, teeth, blood vessels, subsurface area of semi-conductors, chip manufacturing and sensitive medical equipment. The specimen 116 can be a biological sample or a scattering medium.

At step 518, the data may be transferred to the processor by a USB cable or any other form of computer communication. The data from the camera or array is transferred to a processor 122, which is typically a desk-top computer. The processor could also be a tablet computer or a lap-top computer or a desktop computer or a smart phone or a phone or a watch, or a smart watch, or an embedded system per an embodiment of the invention. The data may be transferred to the processor by a USB cable, or a camera-link cable or an Ethernet cable or a wireless connection such as a blue-tooth connection.

A Michelson interferometer can be built using a photonic integrated circuit using waveguides as described in F. Morichetti, et. al. (2007). The technology is based on $Si_3N_4$ and $SiO_2$ waveguide technology called TriPleX™, which has been developed by LioniX BV (Enschede, The Netherlands) as described in the article above by Morichetti et al. In an embodiment the interferometer sub-assembly 330 can be a photonic integrated circuit. The Photonic integrated circuits can be built using many types of material system by way example, but not by limitation; silica on silicon, lithium niobate electro-optic crystals, Silicon on insulator, many polymers, semiconductor material such as GaAs & InP.

The photonic integrated circuit described in above can comprise of the Michelson interferometer 330, and tunable filter 316. The light source 102, the detector 318, could also be optionally included on the same photonic circuit or the same chip. The isolator 106, the ADC 320 and the processor 122 could also be included in the same integrated circuit or the same chip. The isolator 106, the ADC 320 and the processor 122 and the interferometer could also be built using separate chips, which communicate with each other.

In an embodiment, the interference light beam (124) enters a tunable filter (316) such as a Fabry Perot tunable interference filter. In the tunable filter 316, wavelength division multiplexing of interfered light beam (124) takes place. The multiplexed data enters a high speed detector 318 which converts light into an electronic signal. The signal is digitized by a high-speed analog to digital converter (ADC) 320 for further processing using a Processor (122). Wavelength-division-multiplexing as defined in this invention is a process of separating the input broad-band light into light with narrow-band-wavelengths and outputting them sequentially at different time intervals in a single output fiber.

The processor could also be a tablet computer or a lap-top computer or a desktop computer or a smart phone or a phone or a watch, or a smart watch or an embedded system. The processor could also use a field programmable gate array FPGA or a graphics card or a GPU (graphical processing unit). The data may be transferred to the processor by a USB cable, or a camera-link cable or an Ethernet cable or a wireless connection such as a blue-tooth connection.

DIFFERENT TYPES OF TUNABLE FILTERS (316): Many candidates are available for the tunable filter (316). These include acousto-optic tunable filters, or a tunable interference filter or a grating-based filter or a tunable Fabry-Perot interference filter, etc. The traditional spectral domain OCT systems use a broad-band source and a spectrometer as shown in FIG. 1. However, replacing the spectroscopic detection using the tunable filter and a single detector reduces the cost as we do not need to use a full line-scan camera. Since there is only 1 detector, our invention provides the following advantages: smaller form factor, lower cost, and higher efficiency. The spectroscopic detection system has a finite spectral resolution (typically 0.04-0.06 nm/pixel), causing the reduction in signal strength in deeper regions of the image. The tunable filter can provide a much smaller line-width on the order of 0.01 nm per each tuned wavelength. There are inherent losses in a grating based spectrometer (sometimes as high as 70-90%). Those losses are minimized in the proposed invention. Typical insertion loss in a Fabry-Perot based tunable filter is 2-3 dB.

The line-width (also known as bandwidth) of the tunable filter can be as small as (as an example, not a limitation) 0.005 nm. This bandwidth is typically specified as −3 dB bandwidth, which means the width of the filter where the gain of the filter is the half of that of the gain at the center wavelength.

The tuning range of the filter 316 can typically be 50-200 nm and the scan speed can typically range from 1 kHz till 200 kHz, although there is no minimum or maximum tuning range & speed range requirement per the proposed invention. For example, if the scan-speed is 100 kHz, that means each spectrum is measured at s=100 kHz speed. If the tuning range is R=50 nm, and the line-width (lw) is 0.02 nm, the detector 318 needs to measure 2500 points (p=R/lw) per spectrum. That means the detector 318 would need to detect f1=p*s=250 Mega-samples per second. In order to follow the Nyquist criteria, the detector needs to have a pass-band up to fpb=2*f1=0.5 GHz or more. The ADC 320, need to be able to convert 250 Mega-samples/second or more at typically 8-bits to 12 bits resolution. That would mean the ADC speed would need to be at least 3-Gigabits per second for a 12-bit conversion of 250 Mega-samples/second. The data are treated as spectra measured from a spectrometer. The data are processed in the same way the data are processed in spectral domain OCT system (FIG. 11-13 in U.S. application Ser. No. 13/723,006).

Fabry Perot Tunable Filter: The following is a commercially available tunable filter, which can be used as a tunable filter 316. It is based on Fabry-Perot interferometer. The interferometer cavity is resonating. The wavelength tunability performance is enhanced by very high quality reflector coatings. The device does not have any moving parts and it is shock-resistant. The line-width (also known as bandwidth) of the filter can be as small as (as an example, not a limitation) 0.01 nm. This bandwidth is typically specified as −3 dB bandwidth, which means the width of the filter where the gain of the filter is the half of that of the gain at the center wavelength. The tuning range can typically be 50-200 nm, although there is no minimum or maximum tuning range requirement per the proposed invention. The scan speed can typically range from 1 kHz till 200 kHz, although it is not limited on either end by the proposed invention. The typical power ranges from 1-30 mW, although the invention does not impose any range limitations on power.

Some of the tunable filters (including Fabry Perot tunable filter) also comprise of micro concave poly-carbonate lens that forms a cavity without guiding optics or optical collimation, which results in robust filters. The Fabry-Perot etalon can be a MEMS based filter, which can have highly resonant frequency deformable membranes, permitting rapid tuning of the filter. A Fabry Perot filter can also be designed and built such that the first mirror of the filter can be a flat mirror and the second (opposite) mirror can be a curved mirror. The optical length of the Fabry Perot interferometer can be modulated electrostatically moving either or both the mirrors.

The next we present the design equations for the Fabry-Perot tunable filter. The refractive index of the medium of the filter is denoted by n, and d is the thickness of the filter. The free-spectral range (FSR) is the band of wavelength where the filter is getting tuned. $\lambda_{max}$ is the maximum wavelength of the tuning band, $\lambda_{min}$ is the minimum wavelength of the tuning band, $\lambda_0$ is the center wavelength of the tuning band.

$$FSR = \lambda_{max} - \lambda_{min} = \frac{\lambda_0^2}{2nd}$$

The minimum resolvable wavelength is given by $\Delta\lambda$=FSR/$\Phi$ where $\Phi$ is the Finesse of the filter $$\Phi = \left(\frac{\pi r}{1-r^2}\right).$$

Here r is amplitude (i.e., electric field) reflection coefficient at the either surface of the Fabry-Perot filter.

The filter is typically tuned by either varying the index n or thickness d. For example, the thickness d can be varied using electrostatic actuation. The required variation in d is given by $$d\max - d\min = (\lambda_{max} - \lambda_{min})\frac{m}{2nd}$$

Where m is the order of interference. Typical order can be 1, but higher orders can be used. The d can be varied using resonating action, where a voltage waveform is applied to the surface of a piezoelectric Fabry-Perot cavity.

Programmable grating: In another embodiment, a programmable grating can be used as a tunable filter itself. Such a filter can be used as a tunable filter 316. A broadband light is incident on the grating. By manipulating the spacing between the grooves and the depth of the grooves, a specific wavelength can be transmitted or reflected. The spacing and depth of the grooves is altered rapidly to tune the range of wavelength.

The grating equation is given by $$m\lambda_0 = n_g \Lambda \sin \theta_m$$

$\lambda_0$ is the wavelength of interest, and has the principal maximum intensity at angle $\theta_m$. The programmable grating spacing is $\Lambda$. For simplicity, if we set the grating order to m=1, and select the first order, and focus the diffracted beam onto a fiber, we can build a tunable filter by varying $\Lambda$. A certain amount of blazing would help, although not absolutely necessary. If the blazing angle is B, and the light incident is normal to the grating plane, the reflected light would be at angle −2B radians. The following would be the grating equation, here negative sign means the diffraction order is on the certain side of the grating normal.

$$m\lambda_0 = -n_g \Lambda \sin 2B$$

For example, if $\lambda_0$=800 nm, m=1, B=0.1 radian, the grating refractive index $n_g$=1, ignoring the negative sign, $\Lambda$=4026.8 nm. By changing the grating spacing to $\Lambda$=4031.8 nm, the principal maximum will shift to 801 nm. By changing the grating spacing to $\Lambda$=4027.09 nm, the principal maximum will shift to 800.06 nm. Various mechanisms can be used to change the grating spacing. Altering the spacing, the principal maximum can be shifted. The Rayleigh criterion-separation between of the principal maxima (Width of 2-zeros of the diffraction pattern) is given by $(\Delta\lambda)_{min}$=m$\lambda_0$N, here N is total number of grooves on the grating.

Another mechanism to tune wavelength $\lambda_0$ (i.e., shift $\lambda_0$ for the principal maximum intensity at $\lambda_0$) is to modulate the grating refractive index $n_g$ (i.e., the refractive index of the grating material compared to the refractive index of its surrounding medium).

Grating based tunable filter: The following is the grating equation, where $\lambda_b$ is the Bragg phase matching wavelength (the wavelength which gives the brightest intensity of the diffraction pattern), ng is the refractive index of the grating material, $\Lambda$ is the grating period, $\theta$ is the angle of incidence.

$$\lambda_b = 2n_g \Lambda \cos\theta$$

The wavelength is tuned by rotating the grating with respect to the incident light and hence changing the angle of incidence. In order to create a filter, the grating is mounted by replacing a side of a retroreflector. The retroreflector is rotated to tune the wavelength.

In one embodiment of the instant invention, the tunable filter 316 can be removed from its location in FIG. 3 and placed between the isolator 106 and the coupler arm 104. In another embodiment, the tunable filter 316 can be placed between the light source 102 and the isolator 106. The tunable filter can be a programmable-grating-based-filter or a Fabry Perot tunable filter or a grating based tunable filter or an acousto-optic tunable filter.

The system described by Ohbayashi et al. (U.S. Pat. No. 7,940,398) requires an optical demultiplexer, multiple detectors, multiple analog to digital converters. In contrast, our system requires only 1 detector, and 1 analog to digital converter (320). Wavelength-division-multiplexing as defined in this invention is a process of separating the input broad-band light into light with narrow-band-wavelengths and outputting them sequentially at different time intervals in a single output fiber. Tunable filter 316 as described in the invention can be a programmable-grating-based-filter, acousto-optic tunable filter or a tunable interference filter or a tunable Fabry-Perot interference filter. These filters can be tuned electronically with a high speed to perform wavelength-division-multiplexing as defined in this invention.

Ohbayashi et al. (U.S. Pat. No. 7,940,398) are using AWG (Arrayed-Waveguide Grating). The system described by Ohbayashi et al. (U.S. Pat. No. 7,940,398) cannot work with a single detector and a single analog to digital converter. Their system separates out the input broad-band light into light with narrow-band-wavelengths and outputs these simultaneously in multiple fibers. The demultiplexed output light is incident on multiple detectors and the signals are digitized using multiple analog to digital converters.

In one embodiment, we have proposed an interferometric system where the interferometric signal is detected by sampling the signal at a variety of wavelengths (using wavelength-division-multiplexing) using a tunable filter (316). The filter can be a narrow-band filter. The proposed interferometric system comprises of a light source (102) emitting a source beam; a beam-splitter to split the beam from the light source to generate a reference path and a sample path; a specimen (116) and a means to direct the sample path light to the specimen; the beam-splitter to combine the light backscattered from the specimen and the reference path light to generate an interference light beam. The proposed system further comprises of the interference beam, which is passed through a tunable filter for multiplexing the interference data of the specimen; a detector (318) coupled to the filter for detecting a multiplexed interference data of the specimen; and a processor (122) for processing the signals received from the detector and analyzing data by means of wavelength division multiplexing as defined earlier in the application. The sample arm light is optionally directed to the specimen (116) using a lateral scanning optical delivery system (324) if multi-dimensional measurements are needed instead of a single dimension. Thus, the system may be a detection system or a ranging system. The system may also be a multi-dimensional metrology system by laterally scanning the beam incident on the specimen by means of an optical system (324). The specimen (116) can be any one of retina, skin, anterior segment of the eye, posterior segment of the eye, gastrointestinal tract, lungs, teeth, blood vessels, subsurface area of semiconductors, chip manufacturing and sensitive medical equipment. The specimen 116 can be a biological sample or a scattering medium.

In a nutshell, we are proposing a method, comprising: emitting a beam from a light source; splitting the beam using a beam splitter from the source arm to a reference arm and a sample arm; the sample arm light backscattering from the specimen; interfering the reference arm light with the light backscattered from the specimen at the detector. The method also comprises of measuring the interfered light using a tunable filter at different wavelengths; sensing the beam tuned at various wavelengths using a detector; and processing data sensed using a detector in a processor. Michelson interferometer is a specific example of our interferometer.

In a Michelson interferometric system (e.g., 300 in FIG. 3) a first beam-splitter (e.g., 110 in FIG. 3) to split the beam from the light source to generate a reference path and a sample path is the same as a second beam-splitter (e.g., 110 in FIG. 3) to combine the light backscattered from the specimen and the reference path light to generate an interference beam. The beam splitter directs the reference path light to a reference mirror (114 in FIG. 3) and the sample path light onto the specimen. The backscattered sample arm light from the specimen returns to the same beam splitter (110 in FIG. 3); and the reflected light in the reference arm also returns to the same beam splitter (110 in FIG. 3) to generate the interference light beam. The proposed system further comprises of the interference beam entering the detector arm (124), which is passed through the tunable filter (316) for multiplexing the interference data of the specimen. The beam-splitter (110) can optionally be a fiber-optic coupler. If it is a fiber-optic coupler, the PC 126 can be used to match the polarization in sample and reference arms. If 110 is a fiber-optic coupler, the reference arm path can optionally be an optical fiber terminated by a fiber integrated mirror. This fiber integrated mirror could optionally be a birefringent mirror or a fractional wave mirror (402).

The tunable filter in front of the detector having at least one of a programmable-grating-based filter and a Fabry Perot filter in a Michelson Interferometer apparatus above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

INDUSTRIAL APPLICATIONS

OCT system and apparatus of this instant application is very useful for diagnosis and management of ophthalmic diseases such as retinal diseases and glaucoma etc. Instant innovative OCT diagnostic system leverages advancements in cross technological platforms. This enables us to supply the global market a low-cost, portable, robust OCT imaging tool, which would be affordable to general physicians, optometrists and other health personnel. The Michelson interferometric system presented in this application could be used for the OCT imaging, which includes biological OCT imaging or medical OCT imaging or ophthalmic OCT imaging or corneal OCT imaging or retinal OCT imaging, and the like. According to one more embodiment, the Michelson interferometric system may be a detection system or a ranging system.

What is claimed is:

1. A Michelson interferometric system, comprising:
a broad-band light source emitting a source beam;
a beam-splitter to split the source beam from the light source to generate a reference path and a sample path;
a specimen;
and the sample path light is directed to the specimen;
the beam-splitter combines the light backscattered from the specimen and the reference path light to generate a broad-band interference light beam;
the broad-band interference light beam is passed through a tunable filter for wavelength-division-multiplexing;
wherein the wavelength-division-multiplexing comprises separating the broad-band interference light beam into multiplexed interference data of the specimen;
wherein the multiplexed interference data is comprised of narrow-band light with various center-wavelengths, traveling sequentially at different time intervals;
wherein the detector is coupled to the filter for detecting the multiplexed interference data of the specimen;
a processor for processing the signals received from the detector; and
the tunable filter further comprising a programmable grating.

2. The interferometric system of claim 1, wherein the reference path is an optical fiber terminated by at least one of a fiber integrated mirror, a birefringent mirror and a fractional wave mirror.

3. The interferometric system of claim 1, further comprising a fiber stretcher.

4. The interferometric system of claim 1, wherein the system is at least one of a detection system, a ranging system, an imaging system and a metrology system.

5. The interferometric system of claim 1, wherein the system is a multi-dimensional metrology system comprising laterally scanning the sample path light incident on the specimen using an optical system.

6. The interferometric system of claim 1, wherein the polarization is adjusted in the reference arm to match the polarization in the sample arm to achieve optimal signal strength.

7. The interferometric system of claim 5, wherein the lateral scanning is achieved by at least one of a micro electro mechanical system and a micro-opto-mechanical system.

8. The interferometric system of claim 1, where the wavelength of the tunable filter is tuned by modulating a grating refractive index of the programmable grating.

9. The interferometric system of claim 1, wherein the interferometer comprises of photonic integrated circuits and waveguides.

10. The interferometric system of claim 1, wherein a line-width of the tunable filter is at least 0.005 nm.

11. The interferometric system of claim 1, wherein the signals from the detector are transferred to the processor by at least one of a USB cable, a camera-link cable, an Ethernet cable, a wireless connection, and a blue-tooth connection.

12. The system of claim 1, wherein the specimen is at least one of retina, skin, anterior segment of the eye, gastrointestinal tract, lungs, teeth, blood vessels, subsurface area of semi-conductors, chip manufacturing and sensitive medical equipment.

13. A Michelson interferometry method, comprising:
emitting a source beam from a broad-band light source;
splitting the source beam using a beam splitter, into a reference arm and a sample arm;
the sample arm light backscattering from the specimen;
the reference arm light reflecting from at least one of a fractional wave mirror, a birefringent mirror and a free-space-mirror;
interfering the reference arm light with the sample arm light backscattered from the specimen to generate an interfered light;
wavelength-division-multiplexing the interfered light, which comprises sequentially separating the interfered light into multiplexed data with narrow-band wavelengths using at least one of a grating based tunable filter, a Fabry Perot tunable filter and an acousto-optic-tunable filter;
sensing the multiplexed data tuned at various wavelengths using a detector at different time intervals;
processing the multiplexed data sensed using the detector in a processor.

14. The method of claim 13 wherein the wavelength in the grating based tunable filter is tuned by rotating the grating with respect to the interfered light incident on the grating.

15. The method of claim 13 further comprising of the sample arm light passing through a waveplate in the sample arm.

16. An interferometric apparatus, comprising:
a broad-band light source emitting a source beam;
a beam-splitter to split the source beam, to generate a reference path and a sample path;
a specimen;
the sample path light is directed to the specimen;
the beam-splitter combines the light backscattered from the specimen and the reference path light to generate a broad-band interference light beam;
the broad-band interference light beam is passed through a tunable filter for wavelength-division-multiplexing;
wherein the wavelength-division-multiplexing comprises separating the broad-band interference light beam to generate a multiplexed interference data;
wherein the multiplexed interference data is comprised of narrow-band light with various center-wavelengths, traveling sequentially at different time intervals;
wherein the detector is coupled to the filter for detecting the multiplexed interference data;
a processor for processing the signals received from the detector; and
the tunable filter further comprises a Fabry-Perot interference filter comprising highly resonant frequency deformable membranes, permitting rapid tuning of the filter.

17. The apparatus of claim 16 wherein a voltage is applied to the Fabry-Perot interference filter.

18. The apparatus of claim 16, where at least one of the sample path and the reference path comprise of at least one of $Si_3N4$ and $SiO_2$ waveguides.

19. The apparatus of claim 16, where the interferometric apparatus comprises at least one photonic integrated circuit.

20. The method of claim 13, where the processor comprises of at least one of a graphical processing unit, a tablet computer, a lap-top computer, a desktop computer, a smart phone, a phone, a watch, a smart watch, an embedded system, a field programmable gate array.

\* \* \* \* \*